(12) United States Patent
Kiyoshima et al.

(10) Patent No.: US 8,071,130 B2
(45) Date of Patent: Dec. 6, 2011

(54) SOLID PREPARATION

(75) Inventors: Kenichiro Kiyoshima, Osaka (JP); Kenji Nakamura, Osaka (JP); Tetsuya Kawano, Osaka (JP); Masafumi Misaki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 535 days.

(21) Appl. No.: 12/086,700

(22) PCT Filed: Dec. 21, 2006

(86) PCT No.: PCT/JP2006/326169
§ 371 (c)(1),
(2), (4) Date: Jun. 18, 2008

(87) PCT Pub. No.: WO2007/072992
PCT Pub. Date: Jun. 28, 2007

(65) Prior Publication Data
US 2009/0028939 A1    Jan. 29, 2009

(30) Foreign Application Priority Data
Dec. 22, 2005   (JP) ................................. 2005-370375

(51) Int. Cl.
*A61K 9/24* (2006.01)
*A61K 9/28* (2006.01)

(52) U.S. Cl. ........................................ 424/472; 424/474

(58) Field of Classification Search .................. None
See application file for complete search history.

(56) References Cited

U.S. PATENT DOCUMENTS

| | | | |
|---|---|---|---|
| 6,211,205 | B1 | 4/2001 | Ikeda et al. |
| 6,383,471 | B1 | 5/2002 | Chen et al. |
| 6,451,339 | B2 | 9/2002 | Patel et al. |
| 6,902,744 | B1 | 6/2005 | Kolterman et al. |
| 2004/0147564 | A1 | 7/2004 | Rao et al. |
| 2005/0059810 | A1 | 3/2005 | Maeda et al. |
| 2005/0287207 | A1 | 12/2005 | Koike et al. |
| 2006/0141128 | A1 | 6/2006 | Ohkouchi et al. |
| 2006/0280794 | A1 | 12/2006 | Hamaguchi et al. |
| 2006/0286168 | A1 | 12/2006 | Koike et al. |
| 2007/0010423 | A1 | 1/2007 | Wassermann et al. |
| 2007/0166376 | A1 | 7/2007 | Koike |

FOREIGN PATENT DOCUMENTS

| | | |
|---|---|---|
| EP | 0 749 751 A2 | 12/1996 |
| EP | 1 329 217 A1 | 7/2003 |
| EP | 1329217 A1 * | 7/2003 |
| EP | 1 642 593 A1 | 4/2006 |
| JP | 5-163138 A | 6/1993 |
| RU | 2 177 318 C1 | 12/2001 |
| RU | 2 242 244 C2 | 8/2003 |
| WO | WO 98/36755 A1 | 8/1998 |
| WO | WO 98/57649 A1 | 12/1998 |
| WO | WO 99/03476 A1 | 1/1999 |
| WO | WO 00/06126 A1 | 2/2000 |
| WO | WO 0006126 A1 * | 2/2000 |
| WO | WO 00/28989 A1 | 5/2000 |
| WO | WO 00/41546 A2 | 7/2000 |
| WO | WO 01/35941 A2 | 5/2001 |
| WO | WO 03/066028 A1 | 8/2003 |
| WO | WO 2004/006921 A1 | 1/2004 |
| WO | WO 2004/030700 A1 | 4/2004 |
| WO | WO 2004/067001 A1 | 8/2004 |
| WO | WO 2004/069229 A1 | 8/2004 |
| WO | WO 2004/091587 A1 | 10/2004 |
| WO | WO 2004/108161 A1 | 12/2004 |
| WO | WO 2005009407 A2 * | 2/2005 |
| WO | WO 2005/041962 A1 | 5/2005 |
| WO | WO 2005041962 A1 * | 5/2005 |
| WO | WO 2005/099760 A1 | 10/2005 |
| WO | WO 2005/102290 A1 | 11/2005 |

OTHER PUBLICATIONS

Office Action received May 18, 2010, issued in corresponding Peruvian Application No. 001681-2006/OIN, 14 pages.
Russian Office Action dated Oct. 8, 2010, in corresponding Russian Application No. 2008130074, 6 pages, with English translation, 4 pages.
Brief Chemical Encyclopedia, M., Soviet encyclopedia, 1965, v.4, 506-507.
Office Action dated Aug. 6, 2010, in corresponding Kazakhstan Application No. 2008/1586.1, with English translation, 6 pages.

* cited by examiner

*Primary Examiner* — Susan Tran
(74) *Attorney, Agent, or Firm* — Foley & Lardner LLP

(57) ABSTRACT

The present invention intends to provide a solid preparation which contains an insulin sensitizer and an active ingredient other than an insulin sensitizer, and exhibits dissolution behavior of an insulin sensitizer similar to that of an insulin sensitizer from "a solid preparation containing only an insulin sensitizer as an active ingredient". The solid preparation comprises "a part containing coated particles in which the particles containing an insulin sensitizer are coated with lactose or a sugar alcohol" and "a part containing an active ingredient other than an insulin sensitizer".

9 Claims, No Drawings

US 8,071,130 B2

SOLID PREPARATION

TECHNICAL FIELD

The present invention relates to a solid preparation comprising an insulin sensitizer and an active ingredient other than an insulin sensitizer, which is useful as a diabetic treating agent or the like.

BACKGROUND ART

The following preparations containing an insulin sensitizer such as thiazolidinediones and an active ingredient other than an insulin sensitizer have been reported:

1) a solid preparation comprising an insulin sensitizer, an insulin secretagogue and a surfactant (see WO 2005/041962);

2) a unit-dose pharmaceutical composition for treating non-insulin dependent diabetes mellitus, which comprises a combination of glimepiride and a thiazolidinedione insulin sensitizer, and provides a simultaneous release of each drug at rates similar to those obtained with separate administration of immediate release dosage forms of glimepiride and a thiazolidinedione (see US 2004/0147564 A);

3) a pharmaceutical composition comprising an insulin sensitizer, another antidiabetic agent and a pharmaceutically acceptable carrier, wherein the composition is arranged to provide a modified release of at least one of the insulin sensitizer and the other antidiabetic agent (see WO 00/28989);

4) a solid preparation which comprises particles containing an insulin sensitizer and particles containing a HMG-CoA reductase inhibitor (see WO 2004/108161);

5) a solid preparation which comprises (1) a layer containing an insulin sensitizer, and (2) a layer containing (a) an active ingredient other than an insulin sensitizer, (b) crystalline cellulose having an average particle diameter of 5 to 25 μm, (c) crystalline cellulose having an average particle diameter of 30 to 100 μm and (d) polyvinylpyrrolidone K-90 (see WO 2005/099760);

6) a pharmaceutical composition which comprises an insulin sensitivity enhancer in combination with one or more other antidiabetics whose functional mechanism differs from that of the insulin sensitivity enhancer (see EP 749751 A);

7) a pharmaceutical composition which comprises an insulin sensitizer, an insulin secretagogue and a pharmaceutically acceptable carrier (see WO 98/57649);

8) a pharmaceutical composition comprising an insulin sensitizer, a sub-maximal amount of an insulin secretagogue and a pharmaceutically acceptable carrier (see WO 99/03476);

9) a composition comprising a sulfonylurea antidiabetic agent and a glitazone antidiabetic agent in amounts exhibiting a synergistic effect (see WO 98/36755);

10) a process for producing a coated preparation, comprising coating with a dispersion of pioglitazone hydrochloride in an organic solvent containing a coating base soluble in an organic solvent (see WO 2004/006921);

11) a process for producing a coated preparation, comprising coating with an aqueous dispersion of pioglitazone hydrochloride containing a coating base having low viscosity (see WO 2004/067001); and 12) a solid preparation having hardness of 100 to 400 N, and a phase in which an insulin sensitizer and an active ingredient other than an insulin sensitizer are uniformly dispersed (see WO 2004/030700).

DISCLOSURE OF THE INVENTION

In a solid preparation containing an insulin sensitizer and an active ingredient other than an insulin sensitizer, it is preferable that these effective ingredients exhibit dissolution behavior similar to two kinds of solid preparations independently containing these effective ingredients.

The present inventors have studied dissolution property of both ingredients from a solid preparation containing an insulin sensitizer and an active ingredient other than an insulin sensitizer, and have first found that there is a problem that dissolution of an insulin sensitizer from the solid preparation is influenced by a part containing the active ingredient other than an insulin sensitizer, and is slow as compared with dissolution of an insulin sensitizer from "a solid preparation containing only an insulin sensitizer as an active ingredient".

In order to solve the aforementioned problem, the present inventors have intensively studied and, as a result, have found that, in a solid preparation comprising "(1) a part containing coated particles in which the particles containing an insulin sensitizer are coated with lactose or a sugar alcohol" and "(2) a part containing an active ingredient other than an insulin sensitizer", dissolution behavior of the insulin sensitizer is similar to dissolution behavior of the insulin sensitizer from "a solid preparation containing only an insulin sensitizer as an active ingredient".

That is, the present invention provides:

1) A solid preparation comprising the following part (1) and part (2):

(1) a part containing coated particles in which the particles containing an insulin sensitizer are coated with lactose or a sugar alcohol; and (2) a part containing an active ingredient other than an insulin sensitizer, 2) The solid preparation according to the above 1), wherein the insulin sensitizer is pioglitazone or a salt thereof, 3) The solid preparation according to the above 1), wherein the active ingredient is an insulin secretagogue, 4) The solid preparation according to the above 3), wherein the insulin secretagogue is a sulfonylurea agent, 5) The solid preparation according to the above 4), wherein the sulfonylurea agent is glimepiride, 6) The solid preparation according to the above 1), which is a tablet, 7) The solid preparation according to the above 6), which is a multilayer tablet, 8) The solid preparation according to the above 1), wherein the part (1) is a part containing coated particles in which the particles containing an insulin sensitizer are coated with lactose, 9) The solid preparation according to the above 1), wherein the part (2) is a part containing an insulin secretagogue and a surfactant, 10) The solid preparation according to the above 9), wherein the surfactant is Polysorbate 80, 11) The solid preparation according to the above 1), wherein the amount of lactose or a sugar alcohol coating the particle containing an insulin sensitizer is 5 to 50 parts by weight based on 100 parts by weight of the particle, 12) The solid preparation according to the above 1), which is a multilayer tablet obtained by tableting the part (1) and the part (2) in the form of laminate, 13) The solid preparation according to the above 12), wherein the tableting pressure for the part (1) or part (2) tableted first is 60% or less of the tableting pressure for the part (2) or part (1) tableted next, 14) The solid preparation according to the above 1), wherein the "coated particles in which the particles containing an insulin sensitizer are coated with lactose or sugar alcohol" are a granulated material obtained by granulating an insulin sensitizer, an excipient and a disintegrant with a dispersion of a binder and lactose or a sugar alcohol in a solvent, 15) The solid preparation according to the above 1), wherein the "coated particles in which the particles containing an insulin sensitizer are coated with lactose or sugar alcohol" are a granulated material obtained by granulating an insulin sensitizer, an excipient and an disintegrant sequentially with a dispersion of a binder in a solvent, and a dispersion of a binder and lactose or a sugar alcohol in a solvent, and 16) A coated particle in which a particle containing an insulin sensitizer is coated with lactose or a sugar alcohol.

The solid preparation of the present invention is useful as a diabetic treating agent or the like, and exhibits dissolution behavior (preferably dissolution behavior in the living body) similar to two kinds of solid preparations independently containing an insulin sensitizer and an active ingredient other than an insulin sensitizer.

In particular, the solid preparation of the present invention exhibits dissolution behavior (preferably dissolution behavior in the living body) of an insulin sensitizer similar to dissolution behavior of an insulin sensitizer from "a solid preparation containing only an insulin sensitizer as an active ingredient". Specifically, the solid preparation of the present invention has excellent dissolution property of an insulin sensitizer wherein dissolution of an insulin sensitizer from the solid preparation of the present invention is as fast as dissolution of an insulin sensitizer from "a solid preparation containing only an insulin sensitizer as an active ingredient", as described below in Test Examples. More specifically, the solid preparation of the present invention has an excellent dissolution rate of an insulin sensitizer (preferably, pioglitazone hydrochloride) that is 80% or more at 15 minutes after starting a dissolution test when dissolution of an insulin sensitizer (preferably, pioglitazone hydrochloride) from the solid preparation of the present invention is tested by a paddle method (75 rpm) using 900 mL of a 0.3 M hydrochloric acid/potassium chloride buffer (37° C., pH 2.0), as described below in Test Examples.

The solid preparation of the present invention also has excellent preservation stability and therefore, deterioration with time in the quality (e.g. change with time in color and dissolution behavior) of the solid preparation is not observed.

The solid preparation of the present invention also has excellent productivity, for example, it is produced without sticking to a punch and die, and therefore, the solid preparation of the present invention is suitable for industrial-scale production.

The solid preparation of the present invention also exhibits an excellent property that the variation in dissolution behavior of an insulin sensitizer and/or an active ingredient other than an insulin sensitizer is small between each preparations (e.g. between plural tablets).

MODE FOR CARRYING OUT THE INVENTION

The insulin sensitizer used in the present invention may be any drug that restores the impaired function of an insulin receptor to the original state and thereby improves the insulin resistance. Specific examples of the insulin sensitizer include pioglitazone, rosiglitazone, reglixane, netoglitazone, balaglitazone, edaglitazone, 5-(2,4-dioxothiazolidin-5-ylmethyl)-2-methoxy-N-[4-(trifluoromethyl)benzyl]benzamide (KRP-297), rivoglitazone, FK-614, a compound described in WO 99/58510 (e.g., (E)-4-[4-(5-methyl-2-phenyl-4-oxazolylmethoxy)benzyloxyimino]-4-phenylbutyric acid), tesaglitazar, ragaglitazar, muraglitazar, metaglidasen, naveglitazar, MX-6054, LY-510929, T-131, THR-0921, etc.

Herein, the insulin sensitizer may be in the form of a salt, and examples of such a salt include a pharmacologically acceptable salt such as salts with inorganic bases, salts with organic bases, salts with inorganic acids, salts with organic acids, salts with basic or acidic amino acids, and the like.

Preferable examples of the salts with inorganic bases include salts with alkali metals such as sodium, potassium, etc.; alkaline earth metals such as calcium, magnesium, etc.; aluminum; ammonium; and the like.

Preferable examples of the salts with organic bases include salts with trimethylamine, triethylamine, pyridine, picoline, ethanolamine, diethanolamine, triethanolamine, dicyclohexylamine, N,N-dibenzylethylenediamine, etc.

Preferable examples of the salts with inorganic acids include salts with hydrochloric acid, hydrobromic acid, nitric acid, sulfuric acid, phosphoric acid, etc.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferable examples of the salts with basic amino acids include salts with arginine, lysine, ornithine, etc., and preferable examples of the salts with acidic amino acids include salts with aspartic acid, glutamic acid, etc.

In addition, the insulin sensitizer may be any of anhydrides and hydrates.

The insulin sensitizer is preferably pioglitazone or a salt thereof (preferably hydrochloride), or rosiglitazone or a salt thereof (preferably maleate), more preferably pioglitazone or a salt thereof, and even more preferably pioglitazone hydrochloride.

In the present invention, the insulin sensitizer may be used in combination with two or more kinds thereof at an appropriate ratio.

The content of the insulin sensitizer in the solid preparation of the present invention is, for example, 0.01 to 98 parts by weight, preferably 1 to 90 parts by weight based on 100 parts by weight of the solid preparation of the present invention.

In particular, when the insulin sensitizer is pioglitazone hydrochloride, the content of pioglitazone hydrochloride in the solid preparation of the present invention is preferably 0.01 to 70 parts by weight, and more preferably 2 to 60 parts by weight based on 100 parts by weight of the solid preparation of the present invention.

Examples of the active ingredient other than an insulin sensitizer used in the present invention include a diabetic treating drug, a diabetic complication treating drug, a hyperlipemia treating drug, a hypotensive drug, an anti-obesity drug, a diuretic, an antithrombotic drug, etc. These active ingredients may be a low-molecular compound, or high-molecular protein, polypeptide or antibody, or vaccine or the like. Alternatively, the active ingredient may be used in combination with two or more kinds thereof at an appropriate ratio.

Herein, examples of the diabetic treating drug include an insulin preparation (e.g., animal insulin preparations extracted from pancreas of bovine or swine; human insulin preparations synthesized with genetic engineering using *Escherichia coli* or yeast; insulin zinc; protamine insulin zinc; fragments or derivatives of insulin (e.g., INS-1)), α-glucosidase inhibitors (e.g., voglibose, acarbose, miglitol, emiglitate), biguanide agents [e.g., metformin, buformin, or salts thereof (e.g., hydrochloride, fumalate, succinate)], insulin secretagogues [e.g., sulfonylurea agents (e.g., tolbutamide, glibenclamide, gliclazid, chlorpropamide, tolazamide, acetohexamide, glyclopyamide, glimepiride, glipizide, glybuzole), non-sulfonylurea insulin secretagogues (e.g., repaglinide, nateglinide, mitiglinide or calcium salt hydrate thereof)], GLP-1 receptor agonists [e.g., GLP-1, a GLP-1MR agent, NN-2211, exendin-4, BIM-51077, Aib(8,35)hGLP-1 (7.37)NH$_2$, CJC-1131], dipeptidylpeptidase IV inhibitors (e.g., vildagliptin, saxagliptin, NVP-DPP-278, PT-100, NVP-DPP-728, P32/98, P93/01, TS-021, sitagliptin (MK-431), T-6666), P3 agonists (e.g., AJ-9677), amylin agonists (e.g., pramlintide), phosphotyrosinephosphatase inhibitors (e.g., sodium vanadate), glycogenesis inhibitors (e.g., glycogen phosphorylase inhibitors, glucose-6-phosphatase inhibitors, glucagon antagonists), SGLUT (sodium-glucose cotransporter) inhibitors (e.g., T-1095), 11β-hydroxysteroiddehydrogenase inhibitors (e.g., BVT-3498), adiponectin or agonists thereof, IKK inhibitors (e.g., AS-2868), leptin sensitivity-improving agents, somatostatin receptor agonists (e.g., compounds described in WO 01/25228, WO 03/42204, WO 98/44921, WO 98/45285, WO 99/22735), glucokinase activators (e.g., Ro-28-1675), GPR40 agonists, GIP (Glucose-dependent insulinotropic peptide) and the like.

Examples of the diabetic complication treating drug include aldose reductase inhibitors (e.g., tolrestat, epalrestat, zenarestat, zopolrestat, minalrestat, fidarestat, CT-112, ranirestat (AS-3201)), neurotrophic factors (e.g., NGF, NT-3, BDNF), neurotrophic factor production/secretion promoters [e.g., neurotrophin production/secretion promoters described in WO 01/14372 (e.g., 4-(4-chlorophenyl)-2-(2-methyl-1-imidazolyl)-5-(3-(2-methylphenoxy)propyl)oxazole)], PKC inhibitors (e.g., ruboxistaurin mesylate)), AGE inhibitors (e.g., ALT946, pimagedine, piratoxathin, N-phenacylthiazolium bromide (ALT766), EXO-226, ALT-711, pyridorin, pyridoxamine), reactive oxygen scavengers (e.g., thioctic acid), cerebral vasodilators (e.g., tiapride, mexiletine), somatostatin receptor agonists (e.g., BIM23190), and apoptosis signal regulating kinase-1 (ASK-1) inhibitors.

Example of the hyperlipemia treating drug include HMG-CoA reductase inhibitors (e.g., pravastatin, simvastatin, lovastatin, atorvastatin, fluvastatin, lipantil, cerivastatin, itavastatin, rosuvastatin or salts thereof (e.g., sodium salts, calcium salts)), fibrate compounds (e.g., benzafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate and the like), squalene synthase inhibitors (e.g., compounds described in WO 97/10224, for example, 1-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), ACAT inhibitors (e.g., avasimibe, eflucimibe), anion-exchange resins (e.g., cholestyramine), probucol, nicotinic acid drugs (e.g., nicomol, niceritrol), ethyl icosapentate, phytosterol (e.g., soysterol), γ-oryzanol).

Examples of the hypotensive drug include angiotensin converting enzyme inhibitors (e.g., captopril, enalapril, delapril), angiotensin II antagonists (e.g., losartan, eprosartan, valsartan, telmisartan, irbesartan, tasosartan, olmesartan medoxomil, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, nicardipine, amlodipine, efonidipine), potassium channel openers (e.g., levcromakalim, L-27152, AL 0671, NIP-121), clonidine and the like.

Examples of the anti-obesity drug include anti-obesity drugs acting on the central nervous system [(e.g., dexfenfluramine, fenfluramine, phentermine, sibutramine, amphepramone, dexamphetamine, mazindol, phenylpropanolamine, clobenzorex, MCH receptor antagonists (e.g., SB-568849, SNAP-7941, compounds described in WO 01/82925 and WO 01/87834), neuropeptide γ antagonists (e.g., CP-422935), cannabinoid receptor antagonists (e.g., SR-141716, SR-147778), ghrelin antagonists, 111-hydroxysteroiddehydrogenase inhibitors (e.g., BVT-3498)], pancreatic lipase inhibitors (e.g., orlistat, ATL-962), P3 agonists (e.g., AJ-9677), peptidic anorectics (e.g., leptin, CNTF (ciliary neurotrophic factors)), cholecystokinin agonists (e.g., lintitript, FPL-15849), feeding inhibitors (e.g., P-57), and the like.

Examples of the diuretic include xanthine derivatives (e.g., sodium salicylate and theobromine, calcium salicylate and theobromine), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), an anti-aldosterone drug (e.g., spironolactone, triamterene), a carbonic anhydrase inhibitor (e.g., acetazolamide), a chlorobenzensulfonamide drug (e.g., chlorthalidone, mefruside, indapamide), azosemide, isosorbide, etacrynic acid, piretanide, bumetanide, furosemide, and the like.

Examples of the antithrombotic drug include heparin (e.g., heparin sodium, heparin calcium, dalteparin sodium), warfarin (e.g., warfarin potassium), anti-thrombin drugs (e.g., aragatroban), thrombolytic drugs (e.g., urokinase, tisokinase, alteplase, nateplase, monteplase, pamiteplase), platelet aggregation inhibitors (e.g., ticlopidine hydrochloride), cilostazol, ethyl icosapentate, beraprost sodium, sarpogrelate hydrochloride, and the like.

The active ingredient other than an insulin sensitizer used in the present invention is preferably an insulin secretagogue (preferably a sulfonylurea agent, and more preferably glimepiride) and a HMG-CoA reductase inhibitor (preferably simvastatin), and more preferably an insulin secretagogue (preferably a sulfonylurea agent, and more preferably glimepiride).

The content of the active ingredient other than an insulin sensitizer in the solid preparation of the present invention is, for example, 0.01 to 100 parts by weight, preferably 0.03 to 90 parts by weight based on 100 parts by weight of the solid preparation.

In particular, when the active ingredient other than an insulin sensitizer is an insulin secretagogue (preferably a sulfonylurea agent, and more preferably glimepiride), the content of the insulin secretagogue in the solid preparation of the present invention is preferably 0.01 to 70 parts by weight, and more preferably 0.1 to 60 parts by weight based on 100 parts by weight of the solid preparation of the present invention.

When the active ingredient other than an insulin sensitizer is an HMG-CoA reductase inhibitor (preferably simvastatin), the content of the HMG-CoA reductase inhibitor in the solid preparation of the present invention is preferably 0.01 to 70 parts by weight, and more preferably 0.05 to 60 parts by weight based on 100 parts by weight of the solid preparation of the present invention.

The most preferred combination of an insulin sensitizer and an active ingredient other than an insulin sensitizer in the solid preparation of the present invention is a combination of pioglitazone or a salt thereof (preferably pioglitazone hydrochloride) and an insulin secretagogue (preferably a sulfonylurea agent, and more preferably glimepiride).

Of the "lactose or sugar alcohol" (herein simply referred to as a saccharide in some cases) used in the present invention, examples of the "sugar alcohol" include mannitol, sorbitol, erythritol, xylitol, and maltitol. In particular, mannitol is preferred.

The saccharide is preferably lactose.

The content of the saccharide in the solid preparation of the present invention is, for example, 5 to 90 parts by weight, preferably 10 to 85 parts by weight based on 100 parts by weight of the solid preparation.

The solid preparation of the present invention comprises the following part (1) and part (2):

(1) a part containing coated particles in which the particles containing an insulin sensitizer are coated with lactose or a sugar alcohol; and (2) a part containing an active ingredient other than an insulin sensitizer.

The "part" of the aforementioned part (1) and part (2) means a composition which can exist as an independent entity. That is, although the part (1) and the part (2) are components of the solid preparation of the present invention, they are two compositions which can exist as an entity independent from each other.

The solid preparation of the present invention (including the "particles", the "coated particles" and the "parts" which are components of the solid preparation of the present invention) may contain additives conventionally used in the pharmaceutical technology field. Such additives include excipients, disintegrants, binders, lubricants, coloring agents, pH adjusters, surfactants, stabilizers, corrigents, sweetenings, flavors, fluidizing agents and the like. The amounts used of additives are determined in accordance with quantities conventionally used in the pharmaceutical technology field. Two or more of these additives may be used as a mixture at an appropriate proportion.

Examples of excipients include starches such as corn starch, potato starch, wheat starch, rice starch, partially pregelatinized (α) starch, pregelatinized (α) starch and porous starch; saccharides or sugar alcohols such as lactose, fructose, glucose, mannitol and sorbitol; anhydrous calcium phosphate, crystalline cellulose, precipitated calcium carbonate, calcium silicate, and the like.

Examples of disintegrants include carboxymethylcellulose, carboxymethylcellulose calcium, carboxymethylstarch sodium, croscarmellose sodium, crospovidone, low-substituted hydroxypropylcellulose, hydroxypropyl starch and the like. The amount used of the disintegrant is preferably 0.5 to 25 parts by weight, more preferably 1 to 15 parts by weight based on 100 parts by weight of the solid preparation.

Examples of binders include hydroxypropylcellulose, hydroxypropylmethylcellulose, povidone (polyvinylpyrrolidone), gum arabic powder and the like. The amount used of the binder is preferably 0.1 to 50 parts by weight, more preferably 0.5 to 40 parts by weight based on 100 parts by weight of the solid preparation. A preferred binder is hydroxypropylcellulose.

Suitable examples of lubricants include magnesium stearate, calcium stearate, talc, sucrose fatty acid ester, sodium stearyl fumarate and the like.

Examples of coloring agents include food dyes such as food Yellow No. 5 (sunset yellow, the same as food Yellow No. 6 in the United states), food Red No. 2 and food Blue No. 2; food lake pigments, red ferric oxide, yellow ferric oxide and the like.

Examples of pH adjusters include citrate, phosphate, carbonate, tartrate, fumarate, acetate, amino acid salt and the like.

Examples of surfactants include sodium lauryl sulfate, Polysorbate 80, polyoxyethylene(160)polyoxypropylene (30)glycol, polyoxyethylene hydrogenated castor oil 60 and the like.

Examples of stabilizers include sodium ascorbate, tocopherol, tetrasodium edetate, nicotinic acid amide, cyclodextrins; alkali earth metal salts (e.g., calcium carbonate, calcium hydroxide, magnesium carbonate, magnesium hydroxide, magnesium silicate, magnesium aluminate), butylhydroxyanisole and the like.

Examples of corrigents include ascorbic acid, (anhydrous) citric acid, tartaric acid, malic acid and the like.

Examples of sweetenings include Aspartame, Acesulfame K, thaumatin, saccharin sodium, dipotassium glycyrrhizinate and the like.

Examples of flavors include menthol, peppermint oil, lemon oil, vanillin and the like.

Examples of fluidizing agents include light anhydrous silicic acid, hydrous silicon dioxide and the like. The light anhydrous silicic acid contains hydrous silicon dioxide ($SiO_2 \cdot nH_2O$) (wherein n indicates an integer) as the main constituent and specifically includes Sylysia 320 (trade name; Fuji Silysia Chemical LTD), AEROSIL 200 (trade name, Nippon Aerosil CO., LTD) and the like.

The solid preparation of the present invention (including the "particles", the "coated particles" and the "parts" which are components of the solid preparation of the present invention) can be produced by a method conventionally used in the pharmaceutical technology field.

Examples of such a method include operations such as mixing, granulation, filling into capsules, compression-molding, coating and the like, and appropriate combination of these operations.

Herein, the mixing is performed using a mixer such as a V-shape mixer or a tumbling mixer.

The granulation can be performed by any method of a wet granulation method, a dry granulation method and a heat granulation method. Specifically, the granulation is performed using a high-speed stirring granulator, a fluidizing granulation drier, an extrusion granulator, a roller compactor or the like. After granulation, drying, adjustment of a particle size and the like may be performed, if necessary.

The compression-molding is performed, for example, using a single-punch tableting machine or a rotary tableting machine and usually under a pressure of 1 to 35 $kN/cm^2$ (preferably 5 to 35 $kN/cm^2$).

The coating is performed, for example, using a film coating machine.

The dosage forms of the solid preparation of the present invention include oral preparations such as tablets (including sublingual tablets and intraorally disintegrating tablets), capsules (including soft capsules and microcapsules), powders, granules and troches; and parenteral preparations such as external preparations (for example, transdermal preparations and ointments), suppositories (for example, rectal suppositories and vaginal suppositories) and pellets. These preparations may be controlled-release preparations such as immediate-release preparations or sustained-release preparations (for example, sustained-release microcapsules). The solid preparation of the present invention is preferably a tablet (preferably a multilayer tablet).

The solid preparation of the present invention may be in round form, caplet form, oblong form or the like.

When used herein, the "particles" mean particles having an approximately uniform shape and size which are obtained by granulating raw materials in powdered, massive, solution or melted liquid form by a wet granulation method, a dry granulation method or a heat granulation method. Examples of the "particles" include powders, fine granules and granules, and they preferably have a particle size prescribed in the Japanese Pharmacopoeia $14^{th}$ edition.

That is, in a particle size distribution test for preparations, powders preferably have such a particle size distribution that "all the powders pass through a No. 18 (850 μm) sieve and not more than 5% of total powders remain on a No. 30 (500 μm) sieve". Fine granules are preferably said powders in which "not more than 10% of the total passes through a No. 200 (75 μm) sieve". Granules preferably have such a particle size distribution that "all the granules pass through a No. 10 (1700 μm) sieve, not more than 5% of total granules remain on a No. 12 (1400 μm) sieve, and not more than 15% of total granules pass through a No. 42 (355 μm) sieve".

When used herein, the average particle diameter of the "particles" is usually 44 to 2000 μm, preferably 75 to 1000 μm. Herein, the average particle diameter is measured by, for example, a laser diffraction particle size analyzer (e.g. a SYN-PATEC HELOS-RODOS particle size analyzer).

The "particles", when used herein, may vary in shape or size during a process of producing the solid preparation of the present invention (e.g., in a compression-molding step).

The "particles containing an insulin sensitizer" (herein, abbreviated as "the particle of the present invention" in some cases) contained in the solid preparation of the present invention can be produced by granulating an insulin sensitizer with, if necessary, additives. After granulation, if necessary, drying, adjustment of a particle size and the like may be performed.

The additives are preferably excipients (e.g., lactose), disintegrants (e.g., croscarmellose sodium), binders (e.g., hydroxypropylcellulose) and the like.

The content of an insulin sensitizer in the particle of the present invention is, for example, 0.01 to 100 parts by weight, preferably 0.1 to 90 parts by weight per 100 parts by weight of the particle of the present invention.

In particular, when the insulin sensitizer is pioglitazone hydrochloride, the content of pioglitazone hydrochloride in the particle of the present invention is preferably 0.1 to 100 parts by weight, more preferably 1 to 90 parts by weight per 100 parts by weight of the particle of the present invention.

The particle of the present invention is preferably a granulated material obtained by granulating an insulin sensitizer (preferably pioglitazone hydrochloride), an excipient (preferably lactose) and a disintegrant (preferably croscarmellose sodium) with a dispersion of a binder (preferably hydroxypropylcellulose) in a solvent (e.g., water, acetone, ethyl alcohol, propyl alcohol, or a mixture of them at an appropriate ratio; preferably water). In the granulated material, a disintegrant may be omitted.

The dispersion may be a solution or a suspension. The "dispersion" when used herein includes a solution and a suspension.

The "coated particles in which the particles containing an insulin sensitizer are coated with lactose or a sugar alcohol" (herein, abbreviated as "the coated particle of the present invention" in some cases) contained in the solid preparation of the present invention can be produced by coating the particle of the present invention with a saccharide according to a method conventionally used in the pharmaceutical technology field.

The coated particle of the present invention includes coated particles in which the particle of the present invention is completely (i.e. 100% of the total surface area of the particle of the present invention) coated with a saccharide and coated particles in which the particle of the present invention is partially (e.g., 30% or more, preferably 50% or more of the total surface area of the particle of the present invention) with a saccharide.

The "coated particle of the present invention" includes "a granulated material obtained by granulating an insulin sensitizer and, if necessary, additives with a dispersion of a saccharide and a binder in a solvent (e.g., water, acetone, ethyl alcohol, propyl alcohol, and a mixture of them at an appropriate ratio; preferably water), but does not include "a granulated material obtained by granulating an insulin sensitizer and a saccharide and, if necessary, additives with a dispersion of a binder in a solvent (e.g., water, acetone, ethyl alcohol, propyl alcohol, and a mixture of them at an appropriate ratio)".

In the coated particle of the present invention, the amount of a saccharide coating the particle of the present invention is, for example, 5 to 70 parts by weight, preferably 5 to 50 parts by weight based on 100 parts by weight of the particle of the present invention.

The coated particle of the present invention is preferably:
1) a granulated material obtained by granulating an insulin sensitizer (preferably pioglitazone hydrochloride), an excipient (preferably lactose) and a disintegrant (preferably croscarmellose sodium) with a dispersion of a saccharide and a binder (preferably hydroxypropylcellulose) in a solvent (preferably water);
2) a granulated material obtained by granulating an insulin sensitizer (preferably pioglitazone hydrochloride), an excipient (preferably lactose) and a disintegrant (preferably croscarmellose sodium) sequentially with a dispersion of a binder (preferably hydroxypropylcellulose) in a solvent (preferably water), and a dispersion of a binder (preferably hydroxypropylcellulose) and a saccharide in a solvent (preferably water);
3) a coated particle obtained by granulating an insulin sensitizer (preferably pioglitazone hydrochloride), an excipient (preferably lactose) and a disintegrant (preferably croscarmellose sodium) with a dispersion of a binder (preferably hydroxypropylcellulose) in a solvent (preferably water) and then coating the resulting granulated material with a saccharide; or the like.

When the "coated particle of the present invention" contained in the solid preparation of the present invention is the granulated material of the above 2) or the coated particle of the above 3), the solid preparation of the present invention has excellent effects that the dissolution stability of an insulin sensitizer is high and a change (reduction) in the dissolution with time of an insulin sensitizer is small. Herein, the "change in the dissolution with time" means, for example, a change in the dissolution of the solid preparation of the present invention after storage in a sealed colorless glass bottle at 40° C. for 1 month.

In the granulated materials of the above 1) and the above 2) and the coated particle of the above 3), a disintegrant may be omitted.

An example of the "part containing coated particles in which the particles containing an insulin sensitizer are coated with lactose or a sugar alcohol" contained in the solid preparation of the present invention is a composition obtained by mixing the coated particle of the present invention with additives if necessary, and then compression-molding the mixture if necessary.

The additives include preferably disintegrants (e.g., croscarmellose sodium), lubricants (e.g., magnesium stearate) and the like.

The content of the coated particle of the present invention in the "part containing the coated particle of the present invention" is, for example, 1 to 100 parts by weight, preferably 5 to 90 parts by weight based on 100 parts by weight of the part.

The "part containing the coated particle of the present invention" is preferably a composition comprising the "coated particle of the present invention", a disintegrant (preferably croscarmellose sodium) and a lubricant (preferably magnesium stearate).

An example of the "part containing an active ingredient other than an insulin sensitizer" contained in the solid preparation of the present invention is a composition obtained by mixing an active ingredient other than an insulin sensitizer with additives if necessary, and then compression-molding the mixture if necessary.

The additives include preferably excipients (e.g., lactose, crystalline cellulose), disintegrants (e.g., croscarmellose sodium), binders (e.g., hydroxypropylcellulose), lubricants (e.g., magnesium stearate), surfactants (e.g., Polysorbate 80), stabilizers (e.g., butylhydroxyanisole), corrigents (e.g., anhydrous citric acid), coloring agents (e.g., red ferric oxide, yellow ferric oxide) and the like.

The content of an active ingredient other than an insulin sensitizer in the "part containing an active ingredient other than an insulin sensitizer" is, for example, 0.01 to 100 parts by weight, preferably 0.1 to 90 parts by weight based on 100 parts by weight of the part.

In particular, when the active ingredient other than an insulin sensitizer is an insulin secretagogue (preferably a sulfonylurea agent, and more preferably glimepiride), the content of the insulin secretagogue in the "part containing an active ingredient other than an insulin sensitizer" is preferably 0.01 to 70 parts by weight, and more preferably 0.1 to 60 parts by weight based on 100 parts by weight of the part.

When the active ingredient other than an insulin sensitizer is an HMG-CoA reductase inhibitor (preferably simvastin), the content of the HMG-CoA reductase inhibitor in the "part containing an active ingredient other than an insulin sensitizer" is preferably 0.01 to 70 parts by weight, and more preferably 0.1 to 60 parts by weight based on 100 parts by weight of the part.

The "part containing an active ingredient other than an insulin sensitizer" is preferably a composition comprising an active ingredient other than an insulin sensitizer and additives. The additives include preferably excipients (e.g., lactose, crystalline cellulose), disintegrants (e.g., croscarmellose sodium), binders (e.g., hydroxypropylcellulose), lubricants (e.g., magnesium stearate), surfactants (e.g., polysorbate 80), stabilizers (e.g., butylhydroxyanisole), corrigents (e.g., anhydrous citric acid), coloring agents (e.g., red ferric oxide, yellow ferric oxide) and the like.

A suitable example of the "part containing an active ingredient other than an insulin sensitizer" is "particles containing an active ingredient other than an insulin sensitizer", that is, a composition comprising "a granulated material obtained by granulating an active ingredient other than an insulin sensitizer and additives (e.g., excipient, disintegrant, binder, surfactant, stabilizer, corrigent, coloring agent)" and additives (preferably excipient, disintegrant, lubricant).

Another suitable example of the "part containing an active ingredient other than an insulin sensitizer" is "a part containing an insulin secretagogue and a surfactant".

Herein, the surfactant is preferably Polysorbate 80. The content of the surfactant (preferably Polysorbate 80) in the "part containing an insulin secretagogue and a surfactant" is, for example, 0.05 to 20 parts by weight, preferably 0.2 to 5 part by weight based on 100 parts by weight of the "part containing an insulin secretagogue and a surfactant".

The "part containing an insulin secretagogue and a surfactant" may further contain an excipient (e.g., lactose, crystalline cellulose), a disintegrant (e.g., croscarmellose sodium), a binder (e.g., hydroxypropylcellulose), a lubricant (e.g., magnesium stearate), a coloring agent (e.g., red ferric oxide, yellow ferric oxide) and the like.

The "part containing an active ingredient other than an insulin sensitizer" is particularly preferably a composition comprising "a granulated material obtained by granulating an excipient (preferably lactose, or crystalline cellulose) with a dispersion of an insulin secretagogue (preferably a sulfonylurea agent, and more preferably glimepiride), a surfactant (preferably Polysorbate 80), a coloring agent (preferably red ferric oxide, yellow ferric oxide) and a binder (preferably hydroxypropylcellulose) in a solvent (e.g., water, acetone, ethyl alcohol, propyl alcohol, or a mixture of them at an appropriate ratio; preferably water)", an excipient (preferably crystalline cellulose), a disintegrant (preferably croscarmellose sodium) and a lubricant (preferably magnesium stearate).

The content of an active ingredient other than an insulin sensitizer in the "particle containing an active ingredient other than an insulin sensitizer" is, for example, 0.01 to 100 parts by weight, preferably 0.03 to 90 parts by weight based on 100 parts by weight of the particle.

In particular, when the active ingredient other than an insulin sensitizer is an insulin secretagogue (preferably a sulfonylurea agent, and more preferably glimepiride), the content of the insulin secretagogue in the "particle containing an active ingredient other than an insulin sensitizer" is preferably 0.01 to 70 parts by weight, and more preferably 0.1 to 60 parts by weight based on 100 parts by weight of the particle.

When the active ingredient other than an insulin sensitizer is an HMG-CoA reductase inhibitor (preferably simvastatin), the content of the HMG-CoA reductase inhibitor in the "particle containing an active ingredient other than an insulin sensitizer" is preferably 0.01 to 770 parts by weight, and more preferably 0.1 to 60 parts by weight based on 100 parts by weight of the particle.

The solid preparation of the present invention can be produced by formulating the "part containing the coated particle of the present invention" and the "part containing an active ingredient other than an insulin sensitizer" as obtained above, if necessary, with additives according to a conventional method in the pharmaceutical technology field.

The solid preparation of the present invention is preferably a molded product (e.g., a dry-coated tablet, a multilayer tablet; preferably a multilayer tablet) obtained by compression-molding (preferably tableting) the "part containing the coated particle of the present invention" and the "part containing an active ingredient other than an insulin sensitizer" in the form of laminate. For the purpose of avoiding direct contact of respective parts, an intermediate layer of an inert additive (e.g., excipient) may be provided upon production of the molded product.

The solid preparation of the present invention is more preferably a multilayer tablet obtained by tableting the "part containing the coated particle of the present invention" and the "part containing an active ingredient other than an insulin sensitizer" in the form of laminate. For the purpose of preventing the resulting multilayer tablets from capping and laminating, it is preferable that the tableting pressure for the part tableted first is set lower than the tableting pressure for the part tableted next upon production of the multilayer tablet. Specifically, it is preferable that the tableting pressure for the part tableted first (preferably the "part containing an active ingredient other than an insulin sensitizer") is 60% or less (preferably 30% or less) of the tableting pressure for the part tableted next (preferably the "part containing the coated particle of the present invention").

In addition, a capsule obtained by filling the molded product into a capsule (e.g., gelatin capsule), and a preparation obtained by coating the molded product with a coating base are also included in the solid preparation of the present invention.

Herein, examples of a coating base include a sugar-coating base, a water soluble film coating base, an enteric film coating base, sustained-release film coating base and the like.

The sugar-coating base may be white sugar, and may be also used in combination with one or more species selected from talc, precipitated calcium carbonate, gelatin, gum arabic, pullulan, carnauba wax and the like.

Examples of the water soluble film coating base include cellulose polymers such as hydroxypropylcellulose, hydroxypropylmethylcellulose, hydroxyethylcellulose and methylhydroxyethyl cellulose; synthesized polymers such as polyvinylacetal diethylaminoacetate, aminoalkylmethacrylate copolymer E [Eudragit E (trade name)] and polyvinylpyrrolidone; polysaccharides such as pullulan; and the like.

Examples of the enteric film coating base include cellulose polymers such as hydroxypropylmethylcellulose phthalate, hydroxypropylmethylcellulose acetate succinate, carboxymethylethylcellulose and cellulose acetate phthalate; acrylic acid polymers such as methacrylic acid copolymer L [Eudragit L (trade name)], methacrylic acid copolymer LD [Eudragit L-30D55 (trade name)] and methacrylic acid copolymer S [Eudragit S (trade name)]; natural products such as shellac; and the like.

Examples of the sustained-release film coating base include cellulose polymers such as ethyl cellulose and cellulose acetate; acrylic acid polymers such as aminoalkylmethacrylate copolymer RS [Eudragit RS (trade name)] and ethyl acrylate/methyl methacrylate copolymer suspension [Eudragit NE (trade name)]; and the like.

Two or more of the above-mentioned coating bases may be mixed at an appropriate proportion and then used. In a coating step, coating additives may be also used.

The coating additives include a light-blocking agent and/or a coloring agent such as titanium dioxide, talc, red ferric oxide and yellow ferric oxide; a plasticizer such as polyethylene glycol, triethyl citrate, castor oil and polysorbates; organic acid such as citric acid, tartaric acid, malic acid and ascorbic acid; and the like.

The amount of the coating base used is usually 1 to 30 parts by weight, preferably 2 to 10 parts by weight based on 100 parts by weight of a coating preparation.

The solid preparation of the present invention may be printed with a mark or a letter for discrimination and may have a cleavage line for being divided. When the solid preparation of the present invention is a multilayer tablet, for the purpose of discrimination, respective layers constituting the multilayer tablet may be colored with different colors from each other or only a part of layers constituting the multilayer tablet may be colored.

Further, a capsule obtained by filling the "part containing the coated particles of the present invention" and the "part containing an active ingredient other than an insulin sensitizer" into a capsule (e.g., gelatin capsule) is also included in the solid preparation of the present invention.

The solid preparation of the present invention can be orally or parenterally administered to mammals (for example, mice, rats, rabbits, cats, dogs, bovines, horses, monkeys, human being) safely.

The solid preparation of the present invention is useful as a preventing and treating agent for, for example, diabetes (e.g., type 1 diabetes, type 2 diabetes, gestational diabetes), hyperlipemia (e.g., hypertriglyceridemia, hypercholesterolemia, hypo-high density lipoproteinemia, postprandial hyperlipemia), impaired glucose tolerance (IGT), diabetic complications [e.g., neuropathy, nephropathy, retinopathy, cataract, microangiopathy, osteopenia, diabetic hyperosmolar coma, infections (e.g., respiratory tract infection, urinary tract infection, alimentary canal infection, dermal soft tissue infection, inferior limb infection), diabetic gangrene, xerostomia, hypacusis, cerebrovascular disorder, peripheral blood circulation disorder, etc.], obesity, osteoporosis, cachexia (e.g., cancerous cachexia, tuberculous cachexia, diabetic cachexia, homeopathic cachexia, endocrinopathic cachexia, infectious cachexia, or AIDS-induced cachexia), fatty liver, hypertension, polycystic ovary syndrome, renal, diseases (e.g., diabetic nephropathy, glomerulonephritis, glomerulosclerosis, nephrotic syndrome, hypertensive nephrosclerosis, end-stage renal diseases), muscular dystrophy, myocardial infarction, angina pectoris, cerebrovascular disorder (e.g., cerebral infarction, cerebral stroke), insulin resistant syndrome, syndrome X, dysmetabolic syndrome, hyperinsulinemia, hyperinsulinemia-induced sensory disorder, tumors (e.g., leukemia, breast cancer, prostate cancer, skin cancer), irritable bowel syndrome, acute/chronic diarrhea, inflammatory diseases [e.g., Alzheimer's disease, chronic rheumatoid arthritis, spondylitis deformans, arthritis deformans, lumbago, gout, postoperative or traumatic inflammation, swelling, neuralgia, pharyngitis, cystitis, hepatitis (including nonalcoholic fatty hepatitis), pneumonia, pancreatitis, inflammatory colonic disease, ulcerative colitis], visceral obesity syndrome, or arteriosclerosis (e.g., atherosclerosis).

The solid preparation of the present invention is also useful for secondary prevention of the above-mentioned various diseases (e.g., secondary prevention of cardiovascular events such as myocardial infarction) and inhibition of progression in these diseases (e.g., inhibition of the progression from impaired glucose tolerance to diabetes, or inhibition of the progression to arteriosclerosis in diabetic patients).

A dose of the solid preparation of the present invention may be an effective amount based on an insulin sensitizer and an active ingredient other than an insulin sensitizer contained in the solid preparation.

The effective amount of an insulin sensitizer is usually 0.01 to 500 mg/day, preferably 0.1 to 100 mg/day per adult (60 kg body weight).

In particular, when the insulin sensitizer is pioglitazone hydrochloride, the effective amount of pioglitazone hydrochloride is usually 7.5 to 60 mg/day, preferably 15 to 60 mg/day, as pioglitazone, per adult (60 kg body weight).

When the insulin sensitizer is rosiglitazone maleate, the effective amount of rosiglitazone maleate is usually 1 to 12 mg/day, preferably 2 to 8 mg/day per adult (60 kg body weight).

The effective amount of an active ingredient other than an insulin sensitizer is usually 0.01 to 10000 mg/day, preferably 0.1 to 5000 mg/day per adult (60 kg body weight).

When the active ingredient is an insulin secretagogue, the effective amount of an insulin secretagogue is, for example, usually 0.01 to 10000 mg/day, preferably 0.1 to 5000 mg/day per adult (60 kg body weight).

In particular, when the insulin secretagogue is a sulfonylurea agent (preferably glimepiride), the effective amount of a sulfonylurea agent (preferably glimepiride) is usually 0.1 to 100 mg/day, preferably 1 to 10 mg/day per adult (60 kg body weight).

When the active ingredient is an HMG-CoA reductase inhibitor, the effective amount of an HMG-CoA reductase inhibitor is, for example, usually 0.01 to 500 mg/day, preferably 0.1 to 100 mg/day per adult (60 kg body weight).

In particular, when the HMG-CoA reductase inhibitor is atorvastatin calcium, the effective amount of atorvastatin calcium is usually 1 to 100 mg/day, preferably 5 to 80 mg/day per adult (60 kg body weight).

When the HMG-CoA reductase inhibitor is pravastatin sodium, the effective amount of pravastatin sodium is usually 1 to 100 mg/day, preferably 5 to 50 mg/day per adult (60 kg body weight).

When the HMG-CoA reductase inhibitor is simvastatin, the effective amount of simvastatin is usually 1 to 160 mg/day, preferably 5 to 80 mg/day per adult (60 kg body weight).

The solid preparation of the present invention is administered preferably once or twice a day, more preferably once a day to the above-mentioned mammals. Particularly, the solid preparation of the present invention is preferably administered once before breakfast to the mammals.

Particularly preferred examples of the solid preparation of the present invention include:
"a tablet (preferably multilayer tablet) containing 16.53 mg of pioglitazone hydrochloride (15 mg of pioglitazone) and 1 mg of glimepiride per tablet";
"a tablet (preferably multilayer tablet) containing 16.53 mg of pioglitazone hydrochloride (15 mg of pioglitazone) and 3 mg of glimepiride per tablet";
"a tablet (preferably multilayer tablet) containing 16.53 mg of pioglitazone hydrochloride (15 mg of pioglitazone) and 4 mg of glimepiride per tablet";
"a tablet (preferably multilayer tablet) containing 33.06 mg of pioglitazone hydrochloride (30 mg of pioglitazone) and 1 mg of glimepiride per tablet";
"a tablet (preferably multilayer tablet) containing 33.06 mg of pioglitazone hydrochloride (30 mg of pioglitazone) and 2 mg of glimepiride per tablet";
"a tablet (preferably multilayer tablet) containing 33.06 mg of pioglitazone hydrochloride (30 mg of pioglitazone) and 3 mg of glimepiride per tablet";
"a tablet (preferably multilayer tablet) containing 33.06 mg of pioglitazone hydrochloride (30 mg of pioglitazone) and 4 mg of glimepiride per tablet"; and
"a tablet (preferably multilayer tablet) containing 49.59 mg of pioglitazone hydrochloride (45 mg of pioglitazone) and 4 mg of glimepiride per tablet".

The solid preparation of the present invention may be used in combination with one or more drugs (hereinafter referred to as concomitant drugs) selected from diabetic treating drugs, diabetic complication treating drugs, hyperlipemia treating drugs, hypotensive drugs, anti-obesity drugs, diuretics and antithrombotic drugs. As these concomitant drugs, those exemplified as the active ingredient are used.

The timing of administration of the solid preparation of the present invention and a concomitant drug is not limited and they may be administered to a subject simultaneously or at staggered times. Alternatively, a single dosage form containing the solid preparation of the present invention and a concomitant drug may be administered to a subject.

A dose of a concomitant drug can be selected appropriately based on the clinical dose. The combination ratio between the solid preparation of the present invention and a concomitant drug can be selected appropriately depending on a subject to be administered, an administration route, disease to be treated, symptoms and a combination of drugs. In the case where a subject to be administered is a human, 0.01 to 100 parts by weight of a concomitant drug may be used per 1 part by weight of the solid preparation of the present invention.

Thus, by using a concomitant drug, superior effects such as 1) enhanced actions of the solid preparation of the present invention and a concomitant drug (synergistic action of the drugs), 2) reduced doses of the solid preparation of the present invention or a concomitant drug (reduction in a dose of a drug as compared with administration of the drug alone) and 3) reduced secondary effects of the solid preparation of the present invention and a concomitant drug can be obtained.

The present invention further provides "a coated particle in which, a particle containing an insulin sensitizer is coated with lactose or a sugar alcohol". The coated particle is useful, for example, as a raw material for the solid preparation of the present invention.

Hereinafter, the present invention will be explained in detail with reference to Examples, Comparative Examples and Test Examples which are not intended to limit the present invention.

In the following Examples and Comparative Examples, products that meet the Japanese Pharmacopoeia 14th Edition or Japanese Pharmaceutical Excipients 2003 were used as various additives such as lactose, hydroxypropylcellulose, croscarmellose sodium, magnesium stearate, crystalline cellulose and Polysorbate 80.

EXAMPLE 1

A mixture of pioglitazone hydrochloride (99.2 g), croscarmellose sodium (13.2 g) and lactose (184.9 g) was granulated by spraying 136.2 g of an aqueous solution of hydroxypropylcellulose (6.81 g) on it in a fluid bed granulator (manufactured by Powrex Corp., Model: LAB-1). The resulting granulated powder was then granulated by spraying a suspension obtained by dispersing lactose (36 g) in 148.6 g of an aqueous solution of hydroxypropylcellulose (7.59 g) on it in a fluid bed granulator (manufactured by Powrex Corp., Model: LAB-1) to obtain pioglitazone hydrochloride-containing granulated powder coated with lactose. To a part (23.18 g) of the granulated powder thus obtained, croscarmellose sodium (0.728 g) and magnesium stearate (0.096 g) were added and mixed to obtain pioglitazone hydrochloride-containing mixed powder.

Glimepiride (2004 g) was dispersed and suspended in 45000 g of an aqueous solution of hydroxypropylcellulose (2250 g) and then mixed with 6750 g of an aqueous 20 (w/w) % Polysorbate 80 solution. A part (48380 g) of the resulting mixture solution was granulated by spraying it on a mixture of lactose (46530 g) and crystalline cellulose (20250 g) in a fluid bed granulator (manufactured by Powrex Corp., Model: WSG-60). The size of a part of the resulting granulated powder was adjusted. A part (63840 g) of the resulting size-adjusted powder was mixed with croscarmellose sodium (4320 g), crystalline cellulose (3600 g) and magnesium stearate (240 g) to obtain glimepiride-containing mixed powder.

The pioglitazone hydrochloride-containing mixed powder (180 mg) and the glimepiride-containing mixed powder (180 mg) were compressed in the form of laminate at a tableting pressure of 10 kN/cm$^2$ (9.5 mmφ flat-faced with beveled edge) using Autograph (manufactured by Shimadzu Corp., Model: AG-50 kN) to obtain a multilayer tablet containing 45 mg of pioglitazone and 4 mg of glimepiride per tablet.

EXAMPLE 2

A mixture of pioglitazone hydrochloride (20430 g), croscarmellose sodium (2706 g) and lactose (30420 g) was granulated by spraying 27920 g of an aqueous solution of hydroxypropylcellulose (1396 g) on it in a fluid bed granulator (manufactured by Powrex Corp., Model: WSG-60) The resulting granulated powder was then granulated by spraying a part (74120 g) of a suspension obtained by dispersing lactose (18720 g) in 75293 g of an aqueous solution of hydroxypropylcellulose (1973 g) on it in a fluid bed granulator (manufactured by Powrex Corp., Model: WSG-60) to obtain pioglitazone hydrochloride-containing granulated powder coated with lactose. The size of a part of the resulting granulated powder was adjusted. A part (66050 g) of the resulting size-adjusted granulated powder was mixed with croscarmellose sodium (2075 g) and magnesium stearate (273.6 g) to obtain pioglitazone hydrochloride-containing mixed powder.

The pioglitazone hydrochloride-containing mixed powder (180 mg) thus obtained and the glimepiride-containing mixed powder (180 mg) obtained in Example 1 were compressed in the form of laminate at a tableting pressure of 1.1 kN/punch for the first layer and a tableting pressure of 9.1 kN/punch for the second layer (9.5 mm$\phi$ flat-faced with beveled edge) using a rotary tableting machine (manufactured by Kikusui Seisakusho Ltd., Model: AQUA 08242L2JI) to obtain a multilayer tablet containing 45 mg of pioglitazone and 4 mg of glimepiride per tablet.

EXAMPLE 3

A mixture of pioglitazone hydrochloride (99.2 g), croscarmellose sodium (13.2 g) and lactose (112.9 g) was granulated by spraying 136.2 g of an aqueous solution of hydroxypropylcellulose (6.81 g) on it in a fluid bed granulator (manufactured by Powrex Corp., Model: LAB-1). The resulting granulated powder was then granulated by spraying a suspension obtained by dispersing lactose (108 g) in 430.6 g of an aqueous solution of hydroxypropylcellulose (7.59 g) on it in a fluid bed granulator (manufactured by Powrex Corp., Model: LAB-1) to obtain pioglitazone hydrochloride-containing granulated powder coated with lactose. A part (23.18 g) of the resulting granulated powder was mixed with croscarmellose sodium (0.728 g) and magnesium stearate (0.096 g) to obtain pioglitazone hydrochloride-containing mixed powder.

The pioglitazone hydrochloride-containing mixed powder (180 mg) thus obtained and the glimepiride-containing mixed powder (180 mg) obtained in Example 1 were compressed in the form of laminate at a tableting pressure of 10 kN/cm$^2$ (9.5 mm$\phi$ flat-faced with beveled edge) using Autograph (manufactured by Shimadzu Corp., Model: AG-50 kN) to obtain a multilayer tablet containing 45 mg of pioglitazone and 4 mg of glimepiride per tablet.

EXAMPLE 4

A mixture of pioglitazone hydrochloride (99.2 g), croscarmellose sodium (13.2 g) and lactose (148.9 g) was granulated by spraying a suspension obtained by dispersing lactose (72.4 g) in 425.8 g of an aqueous solution of hydroxypropylcellulose (14.4 g) on it to obtain pioglitazone hydrochloride-containing granulated powder coated with lactose. A part (326.8 g) of the resulting granulated powder was mixed with croscarmellose sodium (10.3 g) and magnesium stearate (1.35 g) to obtain pioglitazone hydrochloride-containing mixed powder.

The pioglitazone hydrochloride-containing mixed powder (180 mg) thus obtained and the glimepiride-containing mixed powder (180 mg) obtained in Example 1 were compressed in the form of laminate at a tableting pressure of 10 kN/cm$^2$ (9.5 mm$\phi$ flat-faced with beveled edge) using Autograph (manufactured by Shimadzu Corp., Model: AG-50 kN) to obtain a multilayer tablet containing 45 mg of pioglitazone and 4 mg of glimepiride per tablet.

EXAMPLE 5

A mixture of pioglitazone hydrochloride (99.2 g), croscarmellose sodium (13.2 g) and lactose (148.9 g) was granulated by spraying 136.2 g of an aqueous solution of hydroxypropylcellulose (6.81 g) in a fluid bed granulator (manufactured by Powrex Corp., Model: LAB-1). The resulting granulated powder was then granulated by spraying a suspension obtained by dispersing mannitol (72 g) in 289.6 g of an aqueous solution of hydroxypropylcellulose (7.59 g) on it in a fluid bed granulator (manufactured by Powrex Corp., Model: LAB-1) to obtain a pioglitazone hydrochloride-containing granulated powder coated with mannitol. A part (23.18 g) of the resulting granulated powder was mixed with croscarmellose sodium (0.728 g) and magnesium stearate (0.096 g) to obtain pioglitazone hydrochloride-containing mixed powder.

The pioglitazone hydrochloride-containing mixed powder (180 mg) thus obtained and the glimepiride-containing mixed powder (180 mg) obtained in Example 1 were compressed in the form of laminate at a tableting pressure of 10 kN/cm$^2$ (9.5 mm$\phi$ flat-faced with beveled edge) using Autograph (manufactured by Shimadzu Corp., trade name: AG-50 kN) to obtain a multilayer tablet containing 45 mg of pioglitazone and 4 mg of glimepiride per tablet.

EXAMPLE 6

The pioglitazone hydrochloride-containing mixed powder (120 mg) obtained in Example 2 and the glimepiride-containing mixed powder (90 mg) obtained in Example 1 were compressed in the form of laminate at a tableting pressure of 0.6 kN/punch for the first layer and a tableting pressure of 6.9 kN/punch for the second layer (8.0 mm$\phi$ convex-faced) using a rotary tableting machine (manufactured by Kikusui Seisakusho Ltd., Model: AQUA 08242L2JI) to obtain a multilayer tablet containing 30 mg of pioglitazone and 2 mg of glimepiride per tablet.

EXAMPLE 7

A mixture of pioglitazone hydrochloride (99.2 g), croscarmellose sodium (18 g) and lactose (231.3 g) was granulated by spraying 180 g of an aqueous solution of hydroxypropylcellulose (9 g) on it in a fluid bed granulator (manufactured by Powrex Corp., Model: LAB-1). The resulting granulated powder was then granulated by spraying a suspension obtained by dispersing lactose (96 g) in 388.2 g of an aqueous solution of hydroxypropylcellulose (10.2 g) on it in a fluid bed granulator (manufactured by Powrex Corp., Model: LAB-1) to obtain a pioglitazone hydrochloride-containing granulated powder coated with lactose. Two batches of the resulting granulated powder were subjected to size adjustment. A part (896.4 g) of the resulting size-adjusted powder was mixed with croscarmellose sodium (27.8 g) and magnesium stearate (3.71 g) to obtain pioglitazone hydrochloride-containing mixed powder.

Glimepiride (6 g) and yellow ferric oxide (0.192 g) were dispersed and suspended in 270 g of an aqueous solution of hydroxypropylcellulose (13.5 g) and then mixed with 36 g of an aqueous 20 (w/w) % Polysorbate 80 solution. The resulting mixture solution was granulated by spraying it on a mixture of lactose (278.6 g) and crystalline cellulose (120 g) in a fluid bed granulator (manufactured by Powrex Corp., Model: LAB-1). A part (404.9 g) of the resulting granulated powder was mixed with croscarmellose sodium (27.41 g), crystalline cellulose (22.84 g) and magnesium stearate (1.6 g) to obtain glimepiride-containing mixed powder.

The pioglitazone hydrochloride-contained mixed powder (80 mg) and the glimepiride-containing mixed powder (80 mg) were compressed in the form of laminate at a tableting pressure of 1.1 kN/punch for the first layer and a tableting pressure of 5.4 kN/punch for the second layer (7.0 mmφ flat-faced) using a rotary tableting machine (manufactured by Kikusui Seisakusho Ltd., trade name: AQUARIUS 0512LD2AX) to obtain a multilayer tablet containing 15 mg of pioglitazone and 1 mg of glimepiride per tablet.

EXAMPLE 8

A mixture of pioglitazone hydrochloride (1342 g), croscarmellose sodium (178.2 g) and lactose (2006 g) was granulated by spraying 1836 g of an aqueous solution of hydroxypropylcellulose (91.8 g) on it in a fluid bed granulator (manufactured by Powrex Corp., Model: FD-5S). The resulting granulated powder was then granulated by spraying a suspension obtained by dispersing lactose (977.4 g) in 3909.6 g of an aqueous solution of hydroxypropylcellulose (102.6 g) on it in a fluid bed granulator (manufactured by Powrex Corp., Model: FD-5S) to obtain pioglitazone hydrochloride-containing granulated powder coated with lactose. A part of the resulting granulated powder was subjected to size adjustment. A part (3480 g) of the resulting size-adjusted powder was mixed with croscarmellose sodium (109.2 g) and magnesium stearate (10.8 g) to obtain pioglitazone hydrochloride-containing mixed powder.

A mixture of simvastatin (522.1 g), lactose (3078 g), crystalline cellulose (1040 g) and anhydrous citric acid (65 g) was granulated by spraying a solution of hydroxypropylcellulose (156 g), butylhydroxyanisole (1.04 g) and ethyl alcohol (208 g) in water (2600 g) on it in a fluid bed granulator (manufactured by Powrex Corp., Model: FD-5S). A part of the resulting granulated powder was subjected to size adjustment. A part (4226 g) of the resulting size-adjusted powder was mixed with croscarmellose sodium (226 g) and magnesium stearate (67.8 g) to obtain simvastatin-containing mixed powder.

The pioglitazone hydrochloride-containing mixed powder (180 mg) and the simvastatin-containing mixed powder (400 mg) were compressed in the form of laminate at a tableting pressure of 17.7 kN/punch (13.5×8.5 mm, oblong shape) using a rotary tableting machine (manufactured by Kikusui Seisakusho Ltd., Model: AQUA 08242L2JI) to obtain a multilayer tablet.

EXAMPLE 9

A mixture of pioglitazone hydrochloride (20390 g), croscarmellose sodium (2706 g) and lactose (30460 g) was granulated by spraying 27920 g of an aqueous solution of hydroxypropylcellulose (1396 g) on it in a fluid bed granulator (manufactured by Powrex Corp., Model: WSG-60). The resulting granulated powder was then granulated by spraying a part (74120 g) of a suspension obtained by dispersing lactose (18720 g) in 75293 g of an aqueous solution of hydroxypropylcellulose (1973 g) on it in a fluid bed granulator (manufactured by Powrex Corp., Model: WSG-60) to obtain pioglitazone hydrochloride-containing granulated powder coated with lactose. The size of a part of the resulting granulated powder was adjusted. A part (66050 g) of the resulting size-adjusted granulated powder was mixed with croscarmellose sodium (2075 g) and magnesium stearate (273.6 g) to obtain pioglitazone hydrochloride-containing mixed powder.

Glimepiride (1982 g) was dispersed and suspended in 45000 g of an aqueous solution of hydroxypropylcellulose (2250 g) and then mixed with 6750 g of an aqueous 20 (w/w) % Polysorbate 80 solution. A part (48380 g) of the resulting mixture solution was granulated by spraying it on a mixture of lactose (46550 g) and crystalline cellulose (20250 g) in a fluid bed granulator (manufactured by Powrex Corp., Model: WSG-60). The size of a part of the resulting granulated powder was adjusted. A part (63840 g) of the resulting size-adjusted powder was mixed with croscarmellose sodium (4320 g), crystalline cellulose (3600 g) and magnesium stearate (240 g) to obtain glimepiride-containing mixed powder.

The pioglitazone hydrochloride-containing mixed powder (120 mg) and the glimepiride-containing mixed powder (180 mg) were compressed in the form of laminate at a tableting pressure of 0.8 kN/punch for the first layer and a tableting pressure of 10.4 kN/punch for the second layer (9.0 mmφ convex-faced) using a rotary tableting machine (manufactured by Kikusui Seisakusho Ltd., Model: AQUA 08242L2JI) to obtain a multilayer tablet containing 30 mg of pioglitazone and 4 mg of glimepiride per tablet.

EXAMPLE 10

A mixture of pioglitazone hydrochloride (20330 g), croscarmellose sodium (2706 g) and lactose (30520 g) was granulated by spraying 27920 g of an aqueous solution of hydroxypropylcellulose (1396 g) on it in a fluid bed granulator (manufactured by Powrex Corp., Model: WSG-60). The resulting granulated powder was then granulated by spraying a part (74120 g) of a suspension obtained by dispersing lactose (18720 g) in 75293 g of an aqueous solution of hydroxypropylcellulose (1973 g) on it in a fluid bed granulator (manufactured by Powrex Corp., Model: WSG-60) to obtain pioglitazone hydrochloride-containing granulated powder coated with lactose. The size of a part of the resulting granulated powder was adjusted. A part (11588 g) of the resulting size-adjusted granulated powder was mixed with croscarmellose sodium (364 g) and magnesium stearate (48 g) to obtain pioglitazone hydrochloride-containing mixed powder.

Glimepiride (18 g), red ferric oxide (0.024 g) and yellow ferric oxide (0.072 g) were dispersed and suspended in 270 g of an aqueous solution of hydroxypropylcellulose (13.5 g) and then mixed with 36 g of an aqueous 20 (w/w) % Polysorbate 80 solution. The resulting mixture solution was granulated by spraying it on a mixture of lactose (266.7 g) and crystalline cellulose (120 g) in a fluid bed granulator (manufactured by Powrex Corp., Model: LAB-1). A part (383.64 g) of the granulated powder thus obtained was mixed with croscarmellose sodium (25.97 g), crystalline cellulose (21.64 g) and magnesium stearate (1.51 g) to obtain glimepiride-containing mixed powder.

The pioglitazone hydrochloride-containing mixed powder (120 mg) and the glimepiride-containing mixed powder (80 mg) were compressed in the form of laminate at a tableting pressure of 1.4 kN/punch for the first layer and a tableting pressure of 6.4 kN/punch for the second layer (8.0 mmφ flat-faced with beveled edge) using a rotary tableting machine (manufactured by Kikusui Seisakusho Ltd., trade name: AQUARIUS 0512LD2AX) to obtain a multilayer tablet containing 30 mg of pioglitazone and 3 mg of glimepiride per tablet.

EXAMPLE 11

The pioglitazone hydrochloride-containing mixed powder (80 mg) obtained in Example 7 and the glimepiride-containing mixed powder (133 mg) obtained in Example 10 were compressed in the form of laminate at a tableting pressure of 10 kN/cm² (8.0 mmφ flat-faced with beveled edge) using Autograph (manufactured by Shimadzu Corp., Model: AG-50kN) to obtain a multilayer tablet containing 15 mg of pioglitazone and 4 mg of glimepiride per tablet.

COMPARATIVE EXAMPLE 1

A mixture of pioglitazone hydrochloride (29.75 kg), carmellose calcium (3.24 kg) and lactose (68.71 kg) was granulated by spraying 45 kg of an aqueous solution of hydroxypropylcellulose (2.7 kg) on it in a fluid bed granulator (manufactured by Powrex Corp., Model: STRE-M). Three batches (313.2 kg) of the resulting granulated powder were mixed with carmellose calcium (9.72 kg) and magnesium stearate (1.08 kg) to obtain pioglitazone hydrochloride-containing mixed powder.

The pioglitazone hydrochloride-containing mixed powder (180 mg) thus obtained and the glimepiride-containing mixed powder (180 mg) obtained in Example 1 were compressed in the form of laminate at a tableting pressure of 10 kN/cm² (9.5 mmφ flat-faced with beveled edge) using Autograph (manufactured by Shimadzu Seisakusho Corp., Model: AG-50 kN) to obtain a multilayer tablet.

COMPARATIVE EXAMPLE 2

A mixture of pioglitazone hydrochloride (99.2 g), croscarmellose sodium (13.2 g) and lactose (148.9 g) was granulated by spraying 136.2 g of an aqueous solution of hydroxypropylcellulose (6.81 g) on it in a fluid bed granulator (manufactured by Powrex Corp., Model: LAB-1). The resulting granulated powder was then granulated by spraying a solution of sucrose (72 g) in 151.8 g of an aqueous solution of hydroxypropylcellulose (7.59 g) on it in a fluid bed granulator (manufactured by Powrex Corp., Model: LAB-1) to obtain pioglitazone hydrochloride-containing granulated powder coated with sucrose. A part (23.18 g) of the resulting granulated powder was mixed with croscarmellose sodium (0.728 g) and magnesium stearate (0.096 g) to obtain pioglitazone hydrochloride-containing mixed powder.

The pioglitazone hydrochloride-containing mixed powder (180 mg) thus obtained and the glimepiride-containing mixed powder (180 mg) obtained in Example 1 were compressed in the form of laminate at a tableting pressure of 10 kN/cm² (9.5 mmφ flat-faced with beveled edge) using Autograph (manufactured by Shimadzu Seisakusho Corp., Model: AG-50 kN) to obtain a multilayer tablet.

COMPARATIVE EXAMPLE 3

The pioglitazone hydrochloride-containing mixed powder (180 mg) obtained in Comparative Example 1 was compressed using a rotary tableting machine to obtain a tablet containing 45 mg of pioglitazone per tablet.

COMPARATIVE EXAMPLE 4

The pioglitazone hydrochloride-containing mixed powder (120 mg) obtained in Comparative Example 1 was compressed using a rotary tableting machine to obtain a tablet containing 30 mg of pioglitazone per tablet.

TEST EXAMPLE 1

Dissolution of pioglitazone hydrochloride from the tablets of Examples 1 to 7, 9 and 10 and Comparative Examples 1, 3 and 4 was tested by a paddle method (75 rpm) using 900 mL of a 0.3 M hydrochloric acid/potassium chloride buffer (37° C., pH 2.0). Results are shown in Table 1. In Table 1, the average dissolution rate of 6 tablets is shown.

TABLE 1

| Dissolution rate (%) of pioglitazone hydrochloride | | | | |
|---|---|---|---|---|
| | 15 min | 20 min | 30 min | 45 min |
| Comparative Example 1 | 30 | 42 | 76 | 91 |
| Comparative Example 3 | 99 | 99 | 100 | 100 |
| Comparative Example 4 | 100 | 100 | 101 | 101 |
| Example 1 | 99 | 101 | 101 | 101 |
| Example 2 | 100 | 101 | 101 | 100 |
| Example 3 | 101 | 101 | 101 | 101 |
| Example 4 | 98 | 98 | 98 | 98 |
| Example 5 | 103 | 104 | 104 | 104 |
| Example 6 | 101 | 102 | 102 | 102 |
| Example 7 | 104 | 104 | 104 | 105 |
| Example 9 | 102 | 102 | 102 | 102 |
| Example 10 | 106 | 107 | 107 | 107 |

As shown in Table 1, the solid preparation of the present invention was excellent in dissolution property of an insulin sensitizer (pioglitazone hydrochloride). The solid preparation of the present invention also exhibited dissolution behavior of an insulin sensitizer similar to dissolution behavior of an insulin sensitizer from "a solid preparation containing only an insulin sensitizer as an active ingredient" (e.g., tablets of Comparative Examples 3 and 4).

TEST EXAMPLE 2

Dissolution of pioglitazone hydrochloride from the tablet of Example 2 was tested by a paddle method (75 rpm) using 900 mL of a 0.3 M hydrochloric acid/potassium chloride buffer (37° C., pH 2.0) after the tablet was stored in a sealed colorless glass bottle at 40° C. for 1 month. Results are shown in Table 2. In Table 2, the average dissolution rate of 6 tablets is shown.

TABLE 2

| Dissolution rate (%) of pioglitazone hydrochloride | | | | | |
|---|---|---|---|---|---|
| | | 15 min | 20 min | 30 min | 45 min |
| Example 2 | Initial value | 99 | 100 | 100 | 100 |
| | After storage for 1 month at 40° C. | 99 | 99 | 100 | 100 |

As shown in Table 2, the solid preparation of the present invention was excellent in dissolution stability of an insulin sensitizer (pioglitazone hydrochloride). That is, a change with time in dissolution of an insulin sensitizer (pioglitazone hydrochloride) from the solid preparation of the present invention was not observed.

INDUSTRIAL APPLICABILITY

The solid preparation of the present invention is useful as a diabetic treating agent and the like and is excellent in dissolution property of an insulin sensitizer.

The invention claimed is:
1. A solid preparation comprising the following part (1) and part (2):

(1) a part containing coated particles in which particles containing pioglitazone or a salt thereof are coated with lactose; and
(2) a part containing glimepiride,
wherein part (1) the coated particles are a granulated material obtained by granulating pioglitazone or a salt thereof, an excipient and a disintegrant with a dispersion of a binder and lactose in a solvent, and
the amount of lactose coating the particle containing pioglitazone or a salt thereof is 5 to 50 parts by weight based on 100 parts by weight of the particle;
wherein part (2) is a composition comprising a granulated material obtained by granulating an excipient with a dispersion of glimepiride, a surfactant, a coloring agent and a binder in a solvent, said composition also comprising an excipient, a disintegrant and a lubricant; and
said solid preparation is a multilayer tablet obtained by tabletting the part (1) and the part (2) in the form of a laminate.

2. The solid preparation according to claim 1, wherein the part (2) is a part containing glimepiride and a surfactant.

3. The solid preparation according to claim 2, wherein the surfactant is Polysorbate 80.

4. The solid preparation according to claim 1, wherein the tableting pressure for either part (1) or part (2) tableted first is 60% or less of the tableting pressure for part (2) or part (1) tableted next.

5. The solid preparation according to claim 1, wherein the "coated particles in which particles containing pioglitazone or a salt thereof are coated with lactose" are a granulated material obtained by granulating pioglitazone or a salt thereof, an excipient and a disintegrant sequentially with a dispersion of a binder in a solvent, and a dispersion of a binder and lactose in a solvent.

6. The solid preparation according to claim 1, wherein the excipient is lactose or crystalline cellulose.

7. The solid preparation according to claim 1, wherein the surfactant is Polysorbate 80.

8. The solid preparation according to claim 1, wherein the binder is hydroxypropylcellulose.

9. The solid preparation according to claim 1, wherein the solvent is water.

* * * * *